(12) United States Patent
Freyman

(10) Patent No.: US 7,338,468 B2
(45) Date of Patent: *Mar. 4, 2008

(54) CATHETER FOR ENDOLUMINAL DELIVERY OF THERAPEUTIC AGENTS THAT MINIMIZES LOSS OF THERAPEUTIC

(75) Inventor: Toby Freyman, Watertown, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 732 days.

This patent is subject to a terminal disclaimer.

(21) Appl. No.: 10/673,430

(22) Filed: Sep. 30, 2003

(65) Prior Publication Data
US 2004/0064094 A1  Apr. 1, 2004

Related U.S. Application Data

(63) Continuation of application No. 10/015,697, filed on Dec. 17, 2001, now Pat. No. 6,656,155.

(51) Int. Cl.
*A61M 29/00* (2006.01)
(52) U.S. Cl. .................................. 604/103.01
(58) Field of Classification Search ................ 604/103.01–103.03, 264, 97.02, 96.01, 99.04, 604/513
See application file for complete search history.

(56) References Cited

U.S. PATENT DOCUMENTS

| 5,681,281 A | 10/1997 | Vigil et al. |
| 5,713,863 A | 2/1998 | Vigil et al. |
| 6,210,392 B1 | 4/2001 | Vigil et al. |
| 6,638,246 B1 * | 10/2003 | Naimark et al. ............ 604/103 |
| 6,656,155 B2 * | 12/2003 | Freyman ................ 604/103.01 |

FOREIGN PATENT DOCUMENTS

| GB | 1 093 143 A | 11/1967 |
| WO | WO 02 43796 A | 6/2002 |

* cited by examiner

*Primary Examiner*—Kevin C. Sirmons
(74) *Attorney, Agent, or Firm*—Kenyon & Kenyon LLP (57) ABSTRACT

The present invention relates to a device and method for endoluminal delivery of fluid, such as therapeutic fluid, into the vessel wall that minimizes loss of the fluid. In one embodiment, a catheter for delivering fluid or therapeutic into a vessel wall is provided, wherein the catheter has at least one injector for delivering fluid and a sealing mechanism for preventing or minimizing passage of fluid through an unengaged injector.

14 Claims, 13 Drawing Sheets

CATHETER FOR ENDOLUMINAL DELIVERY OF THERAPEUTIC AGENTS THAT MINIMIZES LOSS OF THERAPEUTIC

RELATED APPLICATIONS

This is a continuation of U.S. patent application Ser. No. 10/015,697, filed Dec. 17, 2001 now U.S. Pat. No. 6,656,155, which is incorporated herein in its entirety by reference thereto.

TECHNICAL FIELD

The present invention regards the delivery of therapeutic agents to a target site of an organic vessel. More particularly the invention regards the delivery of a therapeutic agent through injectors engaged with the interior wall of a lumen.

BACKGROUND

The delivery of therapeutic to the interior lumen walls of a diseased vessel is an important, often repeated, procedure in the practice of modern medicine. Therapeutic agents may be used to treat, regenerate, or otherwise affect the interior lumen wall surface or the vessel wall itself. For example, therapeutic agent may be infused into the walls of blood vessels to inhibit or prevent restenosis of plaque within the artery. The delivery of the therapeutic can be completed by injection of the therapeutic, near the target site, through injectors. These injectors, located on the exterior of a balloon catheter inserted into the lumen, engage and embed into the interior wall of a vessel when the balloon is inflated.

Figure 1:
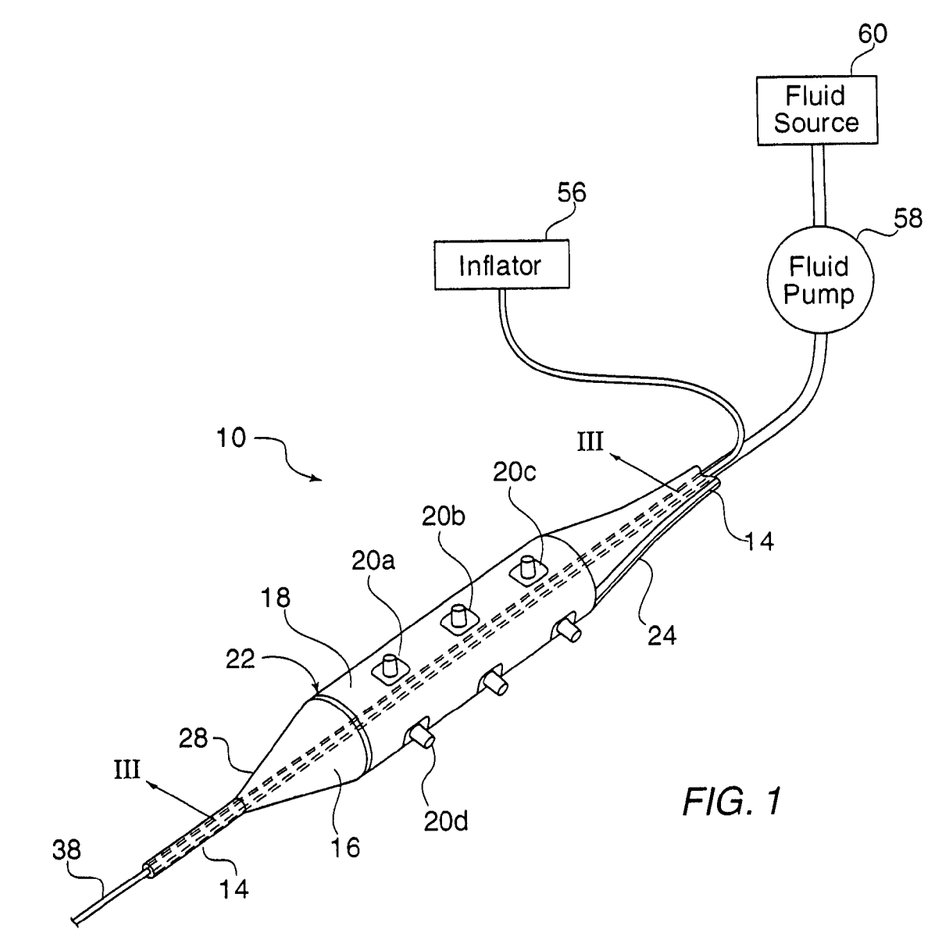
FIG. 1 is a perspective view of a prior therapeutic delivery catheter.
Figure 2:
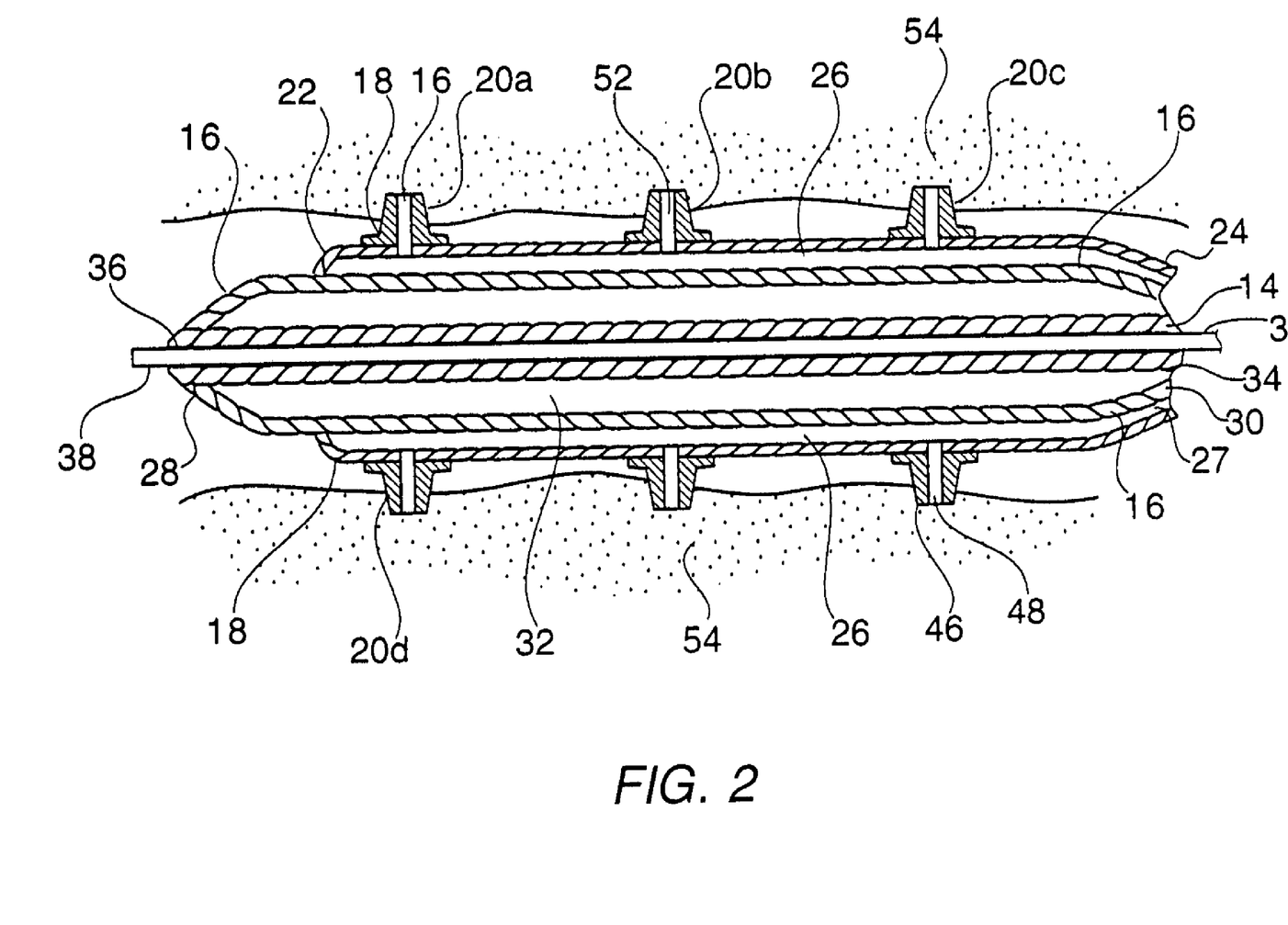
FIG. 2 is an enlarged longitudinal section view of a prior therapeutic delivery catheter taken along line 3-3 of FIG. 1 and positioned in an artery of a patient for delivery of fluid into the vessel wall.

Examples of catheters with therapeutic injectors are shown in U.S. Pat. Nos. 5,681,281; 5,713,863; and 6,210,392, all to Vigil et al. FIGS. 1 and 2, which are taken from U.S. Pat. No. 5,681,281, illustrate such a catheter, defined as device 10. FIG. 2, an enlarged longitudinal section view taken along line 3-3 of FIG. 1, shows injectors, 20a, 20b, 20c, and 20d, engaging and embedding into the interior vessel wall 54 upon inflating balloon 16. With the injectors embedded into the vessel wall, therapeutic is pumped from fluid source 60 (shown in FIG. 1) into the infusion chamber 26 and delivered into the vessel wall through channel 48 of each injector.

Figure 3:
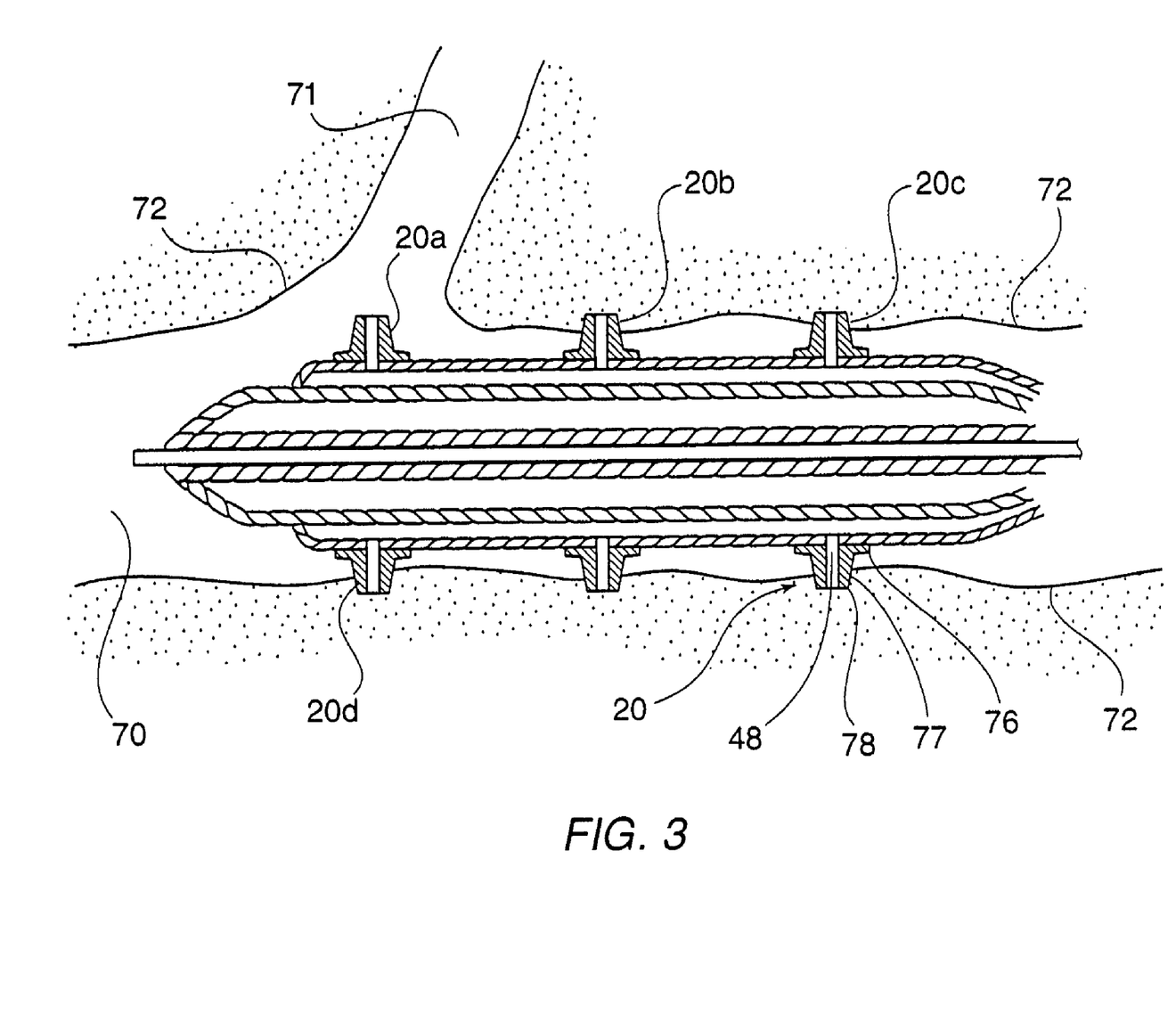
FIG. 3 is an enlarged longitudinal section view of a prior therapeutic delivery catheter taken along line 3-3 of FIG. 1 and positioned in a bifurcated artery of the patient for delivery of fluid into the vessel wall.

None of the above discussed patents, however, addresses the problem of the release of therapeutic directly into the bloodstream from injectors that do not engage the vessel wall. When the diseased or otherwise targeted area is irregularly shaped due to plaque deposits along the interior wall surface, or is near a side vessel or bifurcated branch vessel, the injectors may not engage the vessel wall. For example, FIG. 3 depicts catheter 10 with therapeutic injectors, 20a through 20d, in a bifurcated vessel 70. Bifurcated vessel 70 contains a side vessel branch 71 that prevents injector 20a from embedding into the interior vessel wall 72. As another example, injector 20a of FIG. 4 does not engage or embed into interior vessel wall 73 because the vessel wall is irregularly shaped. Crater 74 of the vessel wall 73 precludes the injector 20a from engaging. Cratered or otherwise irregularly shaped vessel walls are typical in arteries inflicted with arteriosclerosis.

Accordingly, when delivery of therapeutic agent is initiated, the therapeutic released from unengaged injector 20a flows directly into the bloodstream instead of into the walls of the lumen. Due to the toxic nature of some therapeutics, a therapeutic delivery catheter should minimize washing away of therapeutic agents into the blood stream. Further, more therapeutic will flow into the blood stream from an unengaged injector than will be delivered to the vessel wall from an engaged injector because the flow through an engaged injector, such as injectors 20b, 20c, and 20d of FIG. 4, encounters greater resistance, induced by the pressure of interior vessel wall 73, than the unimpeded flow through unengaged injector 20a. Thus, loss of therapeutic through unengaged injectors due to irregularly shaped or bifurcated vessels presents an impediment to the safe and effective delivery of therapeutic agents.

SUMMARY OF THE INVENTION

The present invention regards a catheter for endoluminal delivery of fluid, such as therapeutic fluid, into the vessel wall that minimizes loss of the fluid. In one embodiment, a catheter for delivering fluid or therapeutic into a vessel wall is provided, wherein the catheter has at least one injector for delivering fluid and a sealing mechanism for preventing or minimizing passage of fluid through an unengaged injector.

In an alternative embodiment of the present invention, another catheter for endoluminal delivery of fluid into the vessel wall that minimizes loss of the fluid is provided wherein the catheter has at least one injector for delivering fluid, a sealing mechanism for preventing or minimizing passage of fluid through an unengaged injector, and a combined inflation/infusion chamber for inflating the balloon and infusing the fluid into the vessel wall.

In an alternative embodiment of the present invention, a method for delivering fluid into a vessel wall is provided wherein the method includes inserting a catheter into the vessel of a patient, inflating a balloon by forcing fluid into an inflation chamber to embed an injector into the vessel wall, infusing therapeutic into a vessel wall through the injector by forcing therapeutic fluid into an infusion chamber, and selectively sealing an injector that does not embed into a vessel wall.

In another alternative embodiment of the present invention, another method for delivering fluid into a vessel wall is provided wherein the method includes inserting a catheter into the vessel of a patient, inflating a balloon by forcing fluid into an inflation/infusion chamber to embed an injector into the vessel wall, infusing therapeutic into a vessel wall through the injector by forcing therapeutic fluid into the inflation/infusion chamber, and selectively sealing an injector that does not embed into a vessel wall.

DETAILED DESCRIPTION

As discussed above, FIG. 1 illustrates a prior therapeutic delivery catheter 10 having injectors, 20a through 20d, to deliver therapeutic agents from a therapeutic fluid source 60 into a vessel wall. Therapeutic agents may be used to treat, regenerate, or otherwise affect the interior lumen wall surface or the vessel wall itself. The treated vessel may be any vessel located within or outside of the body of a patient. It may include blood-carrying vessels such as the veins, arteries, and chambers of the heart, it may also include the esophagus, the ureters, the intestines, the pockets of fluid located within the individual vertebrae of the spinal column and any other suitable vessel as apparent to one of skill in the art. Organs and tissues that may be treated by the methods of the present invention include any mammalian tissue or organ, whether located in vivo or ex vivo. Non-limiting examples include the heart, the lungs, the brain, the liver, the kidneys, the bladder, the intestines, the stomach, the pancreas, the ovaries, the prostate, the eyes, as well as tumors, cartilage and bone.

FIG. 2, an enlarged longitudinal section view of prior therapeutic delivery catheter 10 taken along line 3-3 of FIG. 1, shows injectors, 20a, 20b, 20c, and 20d, engaging and embedding into the interior vessel wall 54 upon inflating balloon 16. Balloon 16 is inflated by injecting fluid into inflation chamber 32. With the injectors, 20a through 20d, embedded into the vessel wall 54, therapeutic is pumped from fluid source 60 (shown in FIG. 1) into the infusion chamber 26 and delivered into the vessel wall through channel 48 of each injector.

FIG. 3, another enlarged longitudinal section view of prior therapeutic delivery catheter 10, shows a plurality of injectors 20 comprising a base 76 and a hollow protrusion 77 projecting outward from the base 76 to form a fluid channel 48 traversing the base and hollow protrusion for delivering therapeutic. Of these injectors 20, the injectors defined as 20a, 20b, 20c, and 20d are exemplary. Further, one skilled in the art will appreciate that base 76 can be elongated to accommodate a plurality of hollow protrusions 77. The distal end of hollow protrusion 77 may have a cutting edge 78 formed to assist in penetrating a vessel wall upon engagement. The injector 20 may be made from numerous materials, including stainless steel, plastic, and other suitably rigid polymers. In one embodiment, the injector 20 is made from nickel or a nickel alloy and formed by punching out material from the base 76 forming a hollow protrusion 77 extending outwardly from the base 76.

Figure 4:
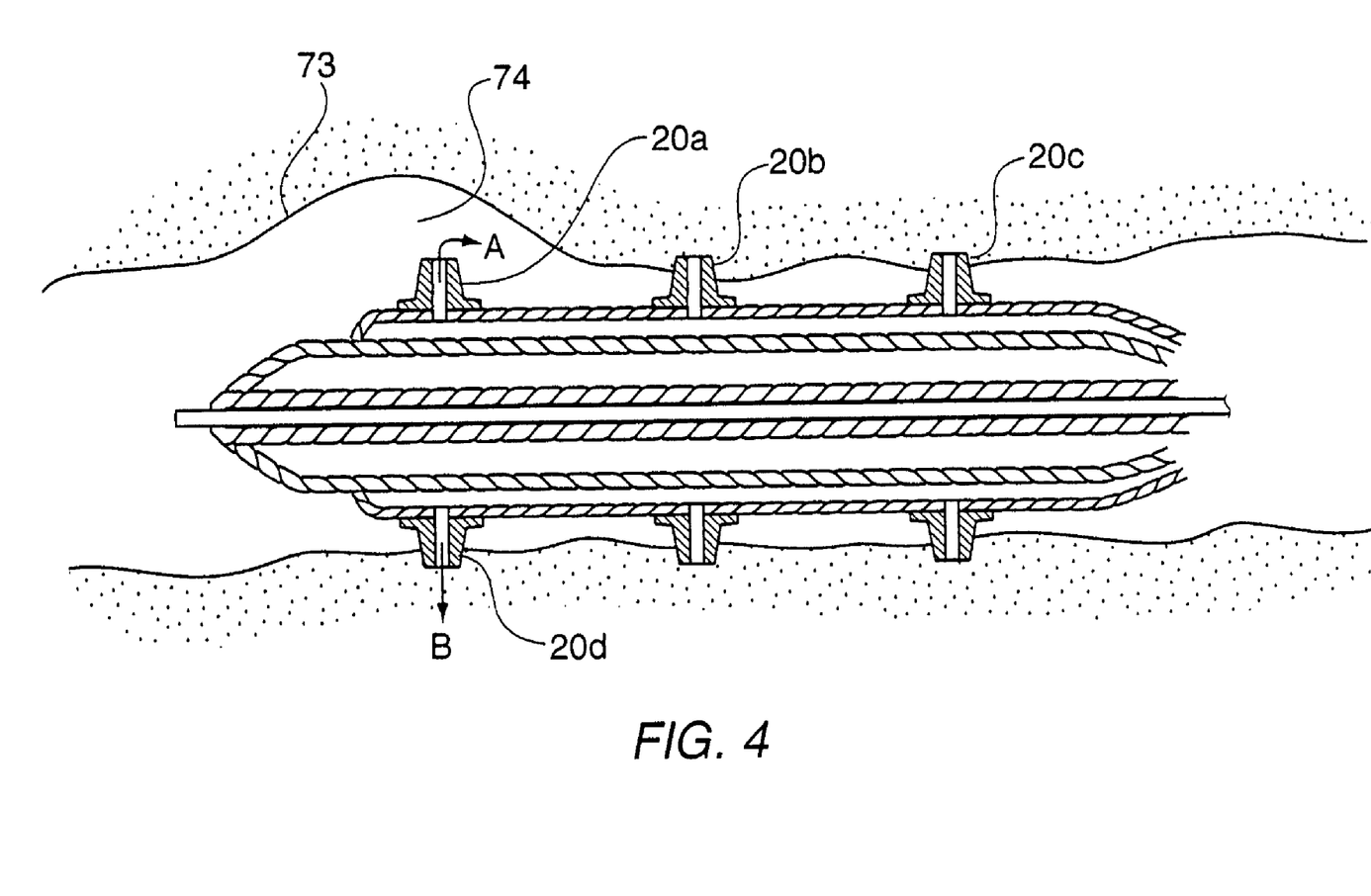
FIG. 4 is an enlarged longitudinal section view of a prior therapeutic delivery catheter taken along line 3-3 of FIG. 1 and positioned in an irregularly shaped artery of the patient for delivery of fluid into the vessel wall.

Prior therapeutic delivery catheters, including the devices described above, did not selectively occlude the flow of therapeutic through the injectors. Accordingly, when the injectors could not engage a vessel wall due to a branch vessel or an irregular shape of the interior vessel wall, therapeutic would flow from the unengaged injector into the blood stream. FIGS. 3 and 4 illustrate problems associated with these prior devices when placed in such a vessel. FIG. 3 is an enlarged longitudinal section view of the catheter 10 taken along line 3-3 of FIG. 1 and positioned in a bifurcated vessel 70 of the patient for delivery of fluid into the vessel wall. As shown in FIG. 3, injectors 20b, 20c, and 20d engage and embed into vessel wall 72. However, bifurcated vessel 70 contains a side vessel branch 71 that prevents injector 20a from embedding into the interior vessel wall 72.

As another example, injector 20a of FIG. 4 does not engage or embed into interior vessel wall 73 because the vessel wall is irregularly shaped. FIG. 4, an enlarged longitudinal section view of the catheter 10 taken along line 3-3 of FIG. 1 and positioned in an irregularly shaped vessel, depicts crater 74 of the vessel wall 73 precluding injector 20a from engaging the vessel wall. Irregularly shaped vessel walls can be caused by built up deposits of plaque on the inside of the vessel wall, by natural physical configuration of the vessel wall, or by calcified deposits located within the vessel wall 73. Calcified deposits can place pressure on the interior lumen wall surface, causing it to deform into an irregular shape. Accordingly, when delivery of therapeutic agent is initiated, the therapeutic released from unengaged injector 20a flows directly into the bloodstream instead of into the walls of the lumen. The flow arrow A demonstrates the direction of flow of therapeutic agent through unengaged injector 20a into the bloodstream. Where the injector 20 engages vessel wall 73, the therapeutic agent is properly released into the vessel wall. The flow arrow B demonstrates the direction of flow of therapeutic agent through engaged injector 20d into the vessel wall 73.

Figure 5:
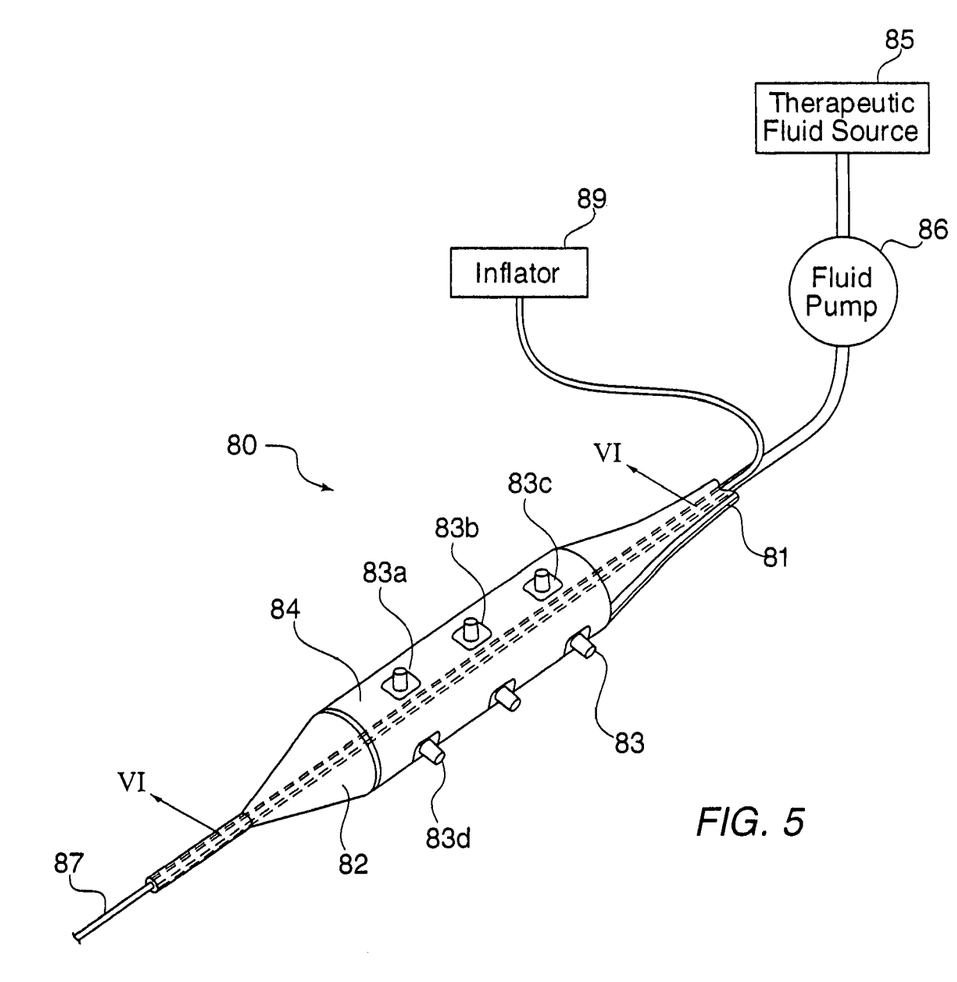
FIG. 5 is a perspective view of the device of the present invention.
Figure 6:
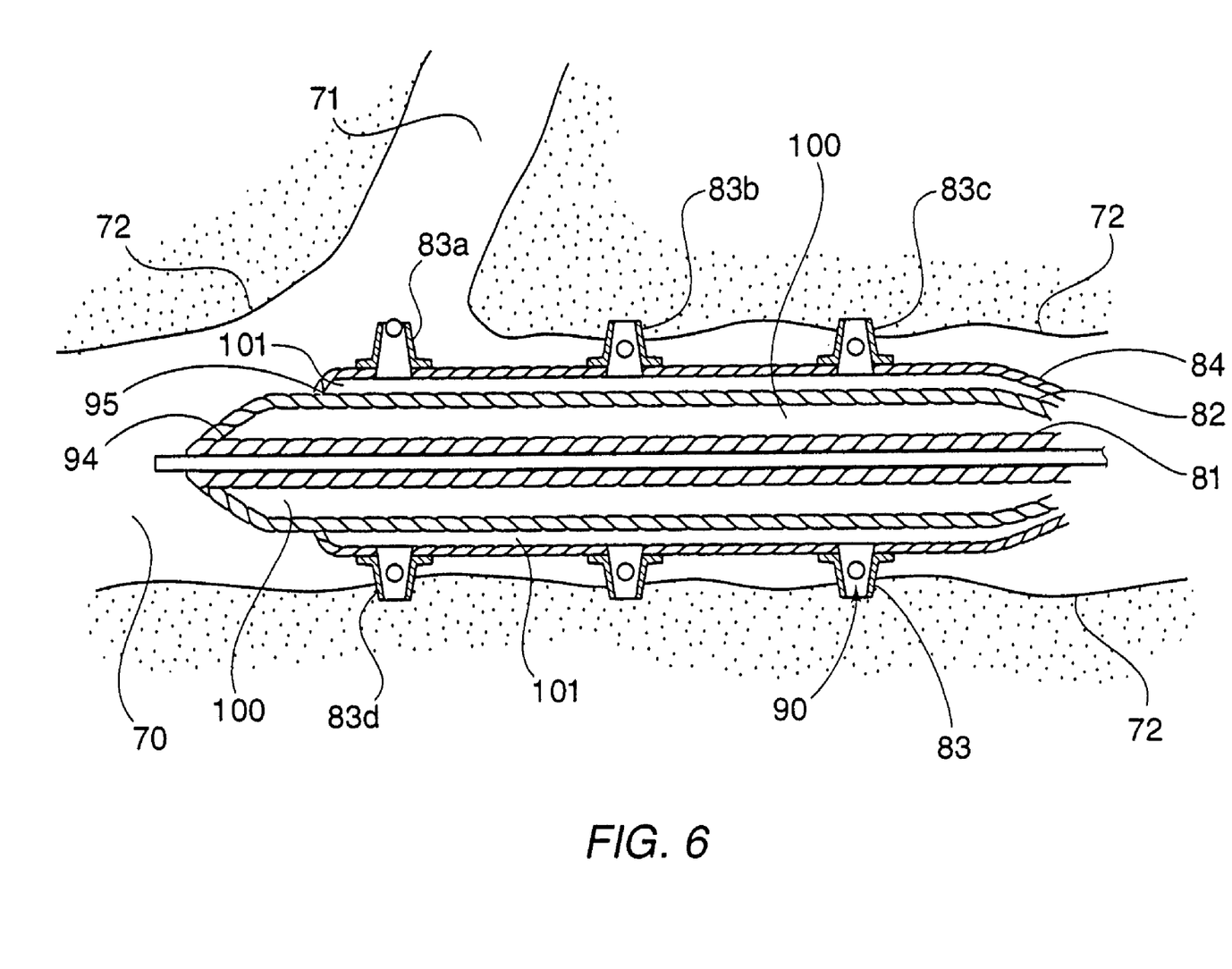
FIG. 6 is an enlarged longitudinal section view of an embodiment of the device of the present invention taken along line 6-6 of FIG. 5 and positioned in a bifurcated artery of the patient for delivery of fluid into the vessel wall.

In FIG. 5, a device in accordance with the present invention for endoluminal delivery of therapeutic agents that minimizes loss of therapeutic is shown and generally designated as 80. As seen in FIG. 5, the components of device 80 include a double-lumen catheter 81 with an inflatable balloon 82 mounted on the exterior surface of catheter 81. FIG. 6 shows inflatable balloon 82 attached at a distal end 94 of catheter 81, thereby creating an inflation chamber 100. Inflation chamber 100 fluidly communicates with the first internal lumen of catheter 81 and an inflator 89 (shown in FIG. 5). A fluid passageway, shown in FIG. 5 as a tubular sleeve 84, surrounds a substantial portion of the inflatable balloon 82, attached at a distal end 95 of inflatable balloon 82, thereby creating an infusion chamber 101. The fluid passageway may be a sleeve that circumferentially surrounds a portion of the inflatable balloon or may be tube strips, with either a substantially round or rectangular internal lumen, placed longitudinally along the exterior surface of the inflatable balloon. The fluid passageway may be flexible or rigid. A plurality of injectors 83 are shown and are mounted on the exterior surface of tubular sleeve 84. Infusion chamber 101 fluidly communicates with the second internal lumen of catheter 81, therapeutic fluid source 85 (shown in FIG. 5), and injectors 83 to deliver therapeutic fluid into the vessel wall. A sealing unit 90 (shown in FIGS. 6 and 7) is included to occlude flow of therapeutic through unengaged injectors 83.

Of these injectors 83, injectors defined as 83a, 83b, 83c, and 83d are exemplary. A skilled artisan will appreciate that the injector 83 can be mounted on balloon 82 in any manner well known in the pertinent art, such as by bonding or other mechanical attachment means. While the illustrated embodiment of device 80 in FIG. 5 discloses rows of three injectors 83 as being evenly and uniformly spaced along tubular sleeve 84, these injectors 83 may be of different sizes or different shapes and may be located at different spacings along the catheter. In this exemplary embodiment, however, these injectors will be evenly spaced along the catheter to facilitate the even distribution of therapeutic into vessel wall. The injectors may be conical in shape, substantially cylindrical in shape, or formed with a substantially conical tip.

Figure 7:
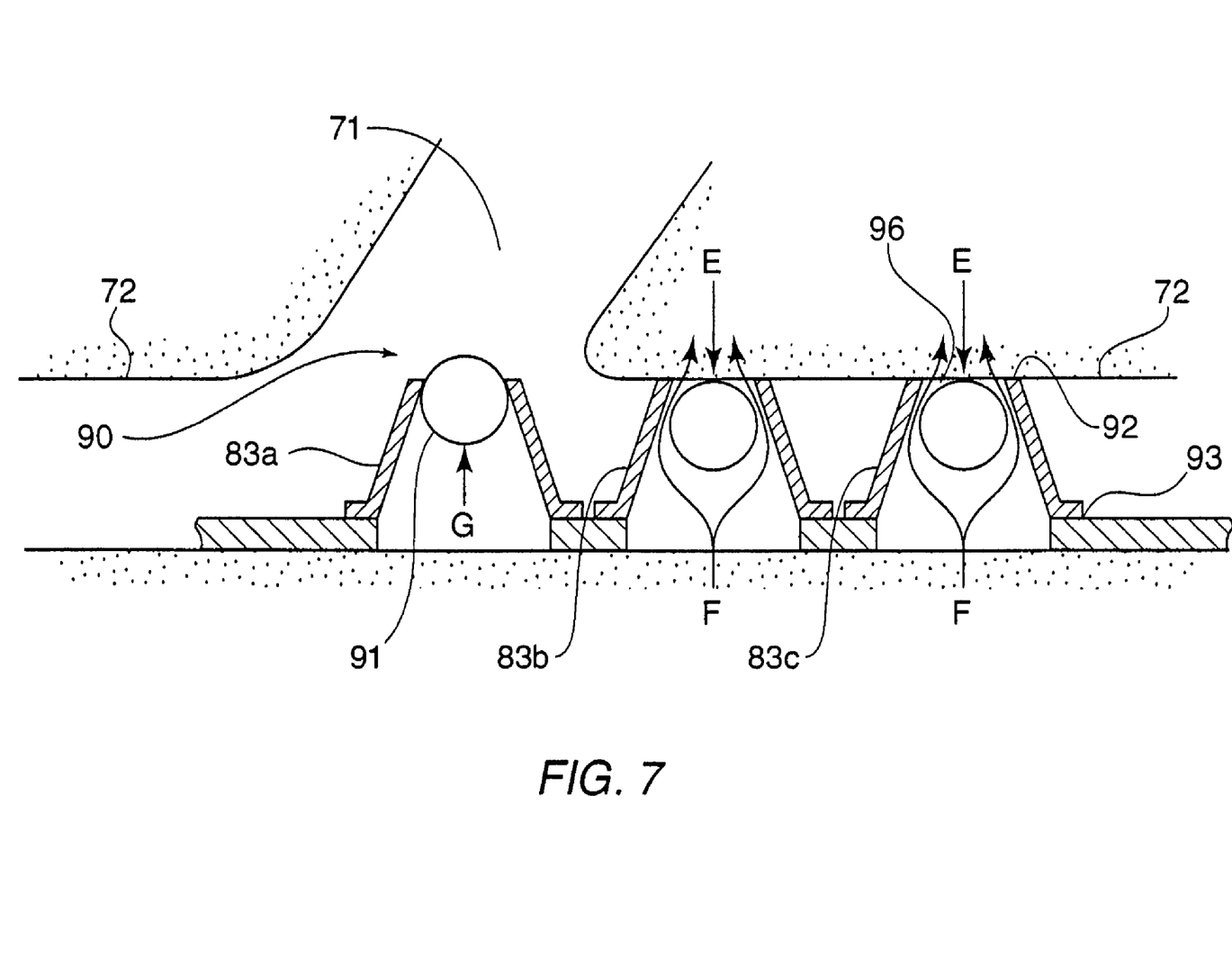
FIG. 7 is an enlarged sectional view of the device of FIG. 6 illustrating the injectors and sealing units positioned in a bifurcated artery of the patient.

FIG. 6 is an enlarged longitudinal section view of the device of the present invention taken along line 6-6 of FIG. 5 and positioned in a bifurcated artery 70 of the patient for delivery of fluid into the vessel wall. Sealing unit 90 controls the flow of therapeutic through injectors 83. FIG. 7, an enlarged sectional view, illustrates injectors 83, and sealing unit 90 comprising seal 91.

In the operation of the device of the present invention, a guidewire 87 (shown in FIG. 5) is first positioned into an artery of the patient to establish a pathway for the therapeutic delivery catheter device 80 to reach the target area. The proximal end of guidewire 87 is then inserted into catheter 81 and the device 80 is advanced over the guidewire to the target area for delivery of therapeutic.

Referring to FIG. 6, delivery of therapeutic is initiated by first inflating the balloon 82 with inflator 89 (shown in FIG. 5) to embed injectors 83 into the vessel wall 72. Inflatable balloon 82, the first internal lumen of catheter 81 and inflator 89 are in fluid communication with each other. Inflator 89, located at the proximal end of catheter 81, may include an inflation fluid source and fluid pump (not shown). Pumping action by the fluid pump causes a bio-compatible non-compressible fluid from the inflation fluid source to be pumped from the proximal end of catheter 81 along the first internal lumen of catheter 81 and expelled into an inflation chamber 100 (shown in FIG. 6), thereby inflating balloon 82 under pressure of the fluid from a first unexpanded diameter to a second expanded diameter.

Inflation fluid source may be a non-toxic fluid source, such as contrast solutions used in ultrasound, fluoroscopy, and MRI procedures, or various brine solutions. The non-toxic inflation fluid source may be utilized for inflating the inflatable balloon to ensure that no toxic fluids, such as some therapeutic fluids, are washed into the bloodstream in the event that the inflatable balloon bursts upon expansion.

Fluid pump may be a syringe or any other pumping means that can apply a pressure on the fluid to carry it into the balloon. These alternative means could include a micro-pump and a collapsible bladder. In a preferred embodiment, the amount of fluid being injected into the catheter, and/or the infusion pressure placed on the fluid, will be measured to help monitor the expansion of the balloon 82 within the lumen 70 and to preclude an overabundance of fluid from being injected into the balloon 82. By measuring the amount of pressure placed on the fluid the operator can monitor the progress of the procedure. In this preferred embodiment, the amount of pressure generated in the vessel will not exceed a known tolerable pressure level for the vessel being treated.

The inflatable balloon 82 may be made with any material that is flexible and resilient. Latex, silicone, polyurethane, rubber (including styrene and isobutylene styrene), and nylon, are each examples of materials that may be used in manufacturing the inflatable balloon. The catheter body 81 may be made from numerous materials, including stainless steel, plastic, and other suitably rigid polymers. It is preferable that the materials used are compatible with the target sites in which they can be used and that they are able to withstand the pressures generated by the fluids passing through them. In addition, they should be flexible enough such that the catheter may be effectively snaked down through a vessel in the body having an irregularly shaped lumen.

As illustrated in FIG. 7, injectors 83b and 83c engage and embed into vessel wall 72 when the inflatable balloon 82 (shown in FIG. 6) is inflated. Upon engagement, the pushing force arrow E demonstrates the direction of a force that may be generated at the distal end 92 of injectors 83, thereby urging the seal 91 to translate from a first position adjacent the distal end 92 of injector 83c, to a second position disposed between the distal and proximal ends, 92 and 93, of injector 83c. Accordingly, an orifice 96 is opened at the distal end 92 of injector 83c. Pumping action of fluid pump 86 pressurizes the therapeutic fluid causing it to flow from therapeutic fluid source 85 (85 and 86 are shown in FIG. 5) along the second internal lumen of catheter 81 into infusion chamber 101, formed between balloon 82 and tubular sleeve 84, and into vessel wall 72 through the opened orifice 96 of engaged and embedded injectors 83b and 83c. Therapeutic flows in the direction indicated by flow arrow F. Fluid pump 86 may be any of the alternate pumping means discussed above.

However, where irregularities of the vessel wall 72 occur, as illustrated by bifurcated side vessel branch 71, causing an injector 83a to not engage and embed into vessel wall 72, sealing unit 90 prevents the flow of therapeutic through an unengaged injector 83. As shown in FIG. 7, injector 83a does not engage and embed into vessel wall 72 because it is positioned at a bifurcated side vessel branch 71. Thus, the vessel wall 72 will not push against seal 91. Accordingly, seal 91 remains in a first position adjacent the distal end 92 of injector 83a and prevents the release of the therapeutic agent directly into the bloodstream from unengaged injectors, thereby minimizing the release of toxic therapeutic agents into the blood stream. Mechanical, chemical, fluid or other forces may be used to maintain seal 91 of unengaged injector 83a in a first position adjacent the distal end 92 of injector 83a, thereby preventing release of therapeutic agent into the bloodstream. Alternative embodiments of these forces are discussed in detail below. The seal 91 in the present embodiment and in alternative embodiments discussed below, may be made from numerous materials, including stainless steel, plastic, and other suitably rigid polymers.

Figure 8:
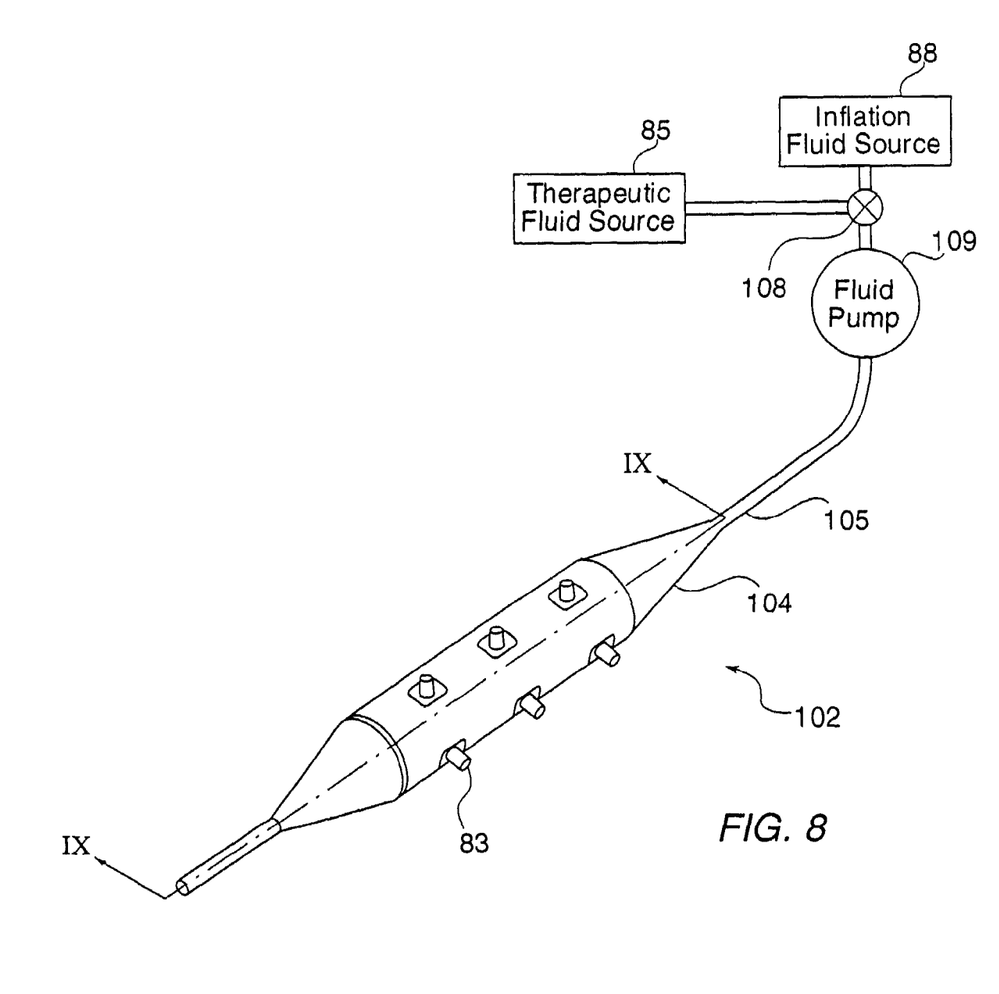
FIG. 8 is a perspective view of an alternative embodiment of the present invention.
Figure 9:
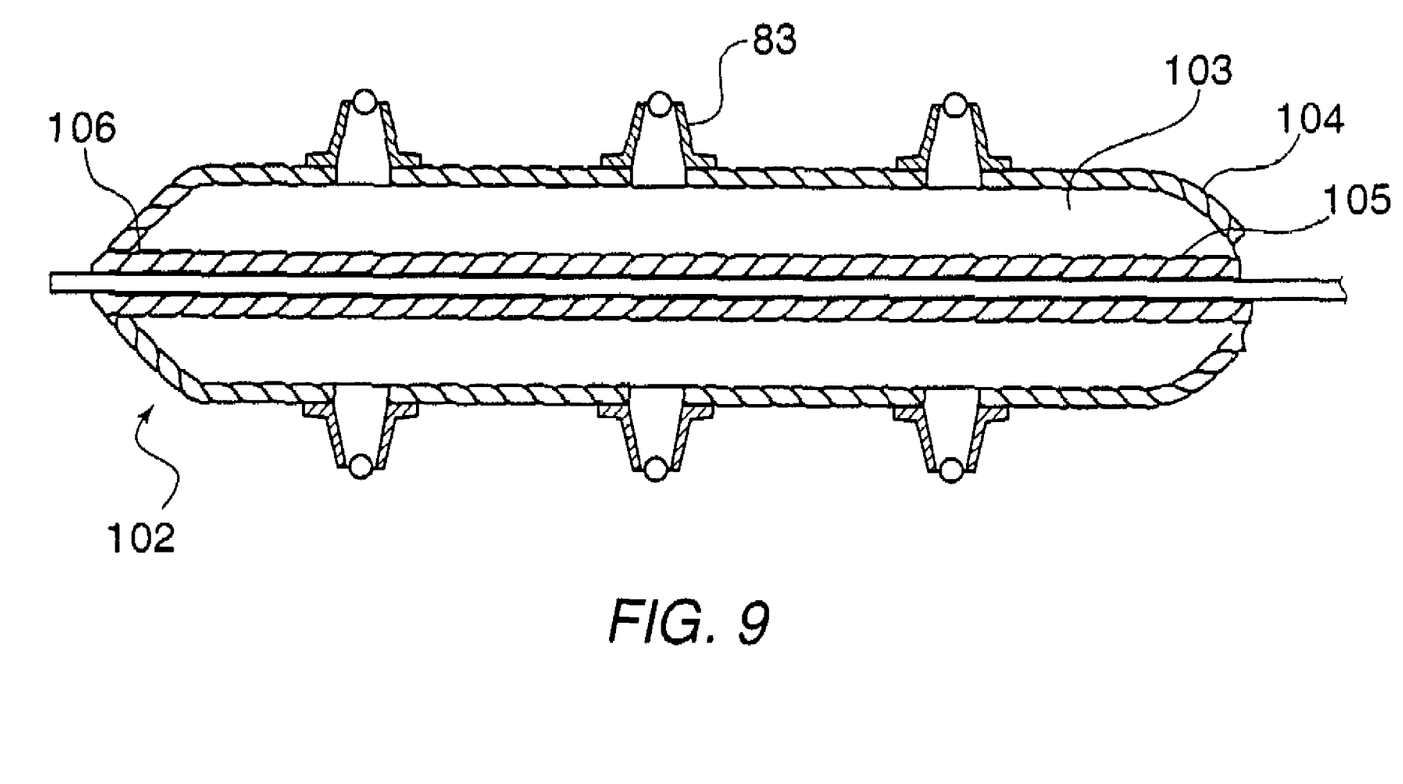
FIG. 9 is an enlarged longitudinal section view of the embodiment of FIG. 8 taken along line 9-9 of FIG. 8.

Rather than have a separate inflation chamber 100 and infusion chamber 101, an alternate embodiment of therapeutic delivery catheter 102, illustrated in FIGS. 8 and 9, may comprise of one inflation/infusion chamber 103.

Because the sealing unit 90 occludes flow through the injectors 83, thereby maintaining the pressure within device 102 while inflating the balloon, the separate inflation and infusion chambers can be combined into a single inflation/infusion chamber. FIG. 8 is a perspective view in accordance with an alternate embodiment 102 of the present invention. FIG. 9 is a longitudinal section view along line 9-9 of FIG. 8. As shown in FIG. 9, an inflatable balloon 104 is mounted on the exterior surface of catheter 105, attached directly to the surface of catheter 105 at the distal end 106 of catheter 105, thereby creating an inflation/infusion chamber 103 of device 102. A plurality of injectors 83 are mounted on the exterior surface of inflatable balloon 104. Sealing units 90 may selectively occlude the flow of fluid through injectors 83 as disclosed above. Inflation/infusion chamber 103 fluidly communicates with an internal lumen of catheter 105, an inflation fluid source 88, a therapeutic fluid source 85 and injectors 83. Valve 108 selectively controls fluid flow into inflation/infusion chamber 103 from inflation fluid source 88 and from therapeutic fluid source 85. A person skilled in the art would appreciate that the valve 108 can be designed in any manner well known in the pertinent art, such as by utilizing a stopcock valve or by other mechanical valve means.

Operation of alternate embodiment of therapeutic delivery catheter 102 begins by inflating inflatable balloon 104 to engage and embed injectors 83 into the vessel wall (not shown). As illustrated in FIG. 8, inflating inflatable balloon 104 from a first unexpanded diameter to a second expanded diameter is achieved by pumping action of fluid pump 109. Valve 108 is selectively opened to permit inflation fluid to flow from inflation fluid source 88, and to preclude therapeutic fluid from flowing from therapeutic fluid source 85. Pumping action of fluid pump 109 pressurizes and causes inflation fluid to be expelled from inflation fluid source 88 into inflation/infusion chamber 103. Seals 91 of sealing units 90 prevent inflation fluid from being expelled into bloodstream through unengaged injectors 83 while inflatable balloon 104 is being inflated. As discussed above, mechanical, chemical, fluid or other forces may be used to maintain seal 91 in a position that occludes the orifice 96 of injectors 83. Also as described above, once the injectors 83 engage and embed into the vessel wall, seal 91 translates away from the vessel wall, and an orifice 96 is opened at the distal end 92 of injector 83. Valve 108 is then selectively opened to permit therapeutic fluid to flow from therapeutic fluid source 85, and to prevent inflation fluid from flowing from inflation fluid source 88. Pumping action of fluid pump 109 then pressurizes and causes therapeutic fluid to be expelled from therapeutic fluid source 85 to the inflation/infusion chamber 103 and into the vessel wall through injector 83.

In another alternate embodiment of the present device (not shown), rather than having two fluid sources—one non-toxic inflation fluid source and one therapeutic fluid source—a single non-toxic or minimally toxic therapeutic fluid source can be used. The single therapeutic fluid source will first serve as the fluid to inflate the balloon and then be expelled into the vessel wall through the injectors once the seal is pushed away from the injector orifice thereby permitting flow into the vessel wall.

A person skilled in the art would appreciate that a variety of seal configurations can be designed to accommodate the variety of injector configurations. In the above embodiments, such as shown in FIG. 7, seal 91 of sealing unit 90 may be spherically shaped to accommodate the conical internal passageway of injector 83. A skilled artisan would also appreciate that using a spherical or similarly round seal helps minimize trauma on the interior wall of the vessel where the possibility of thrombosis is high.

Figure 10:
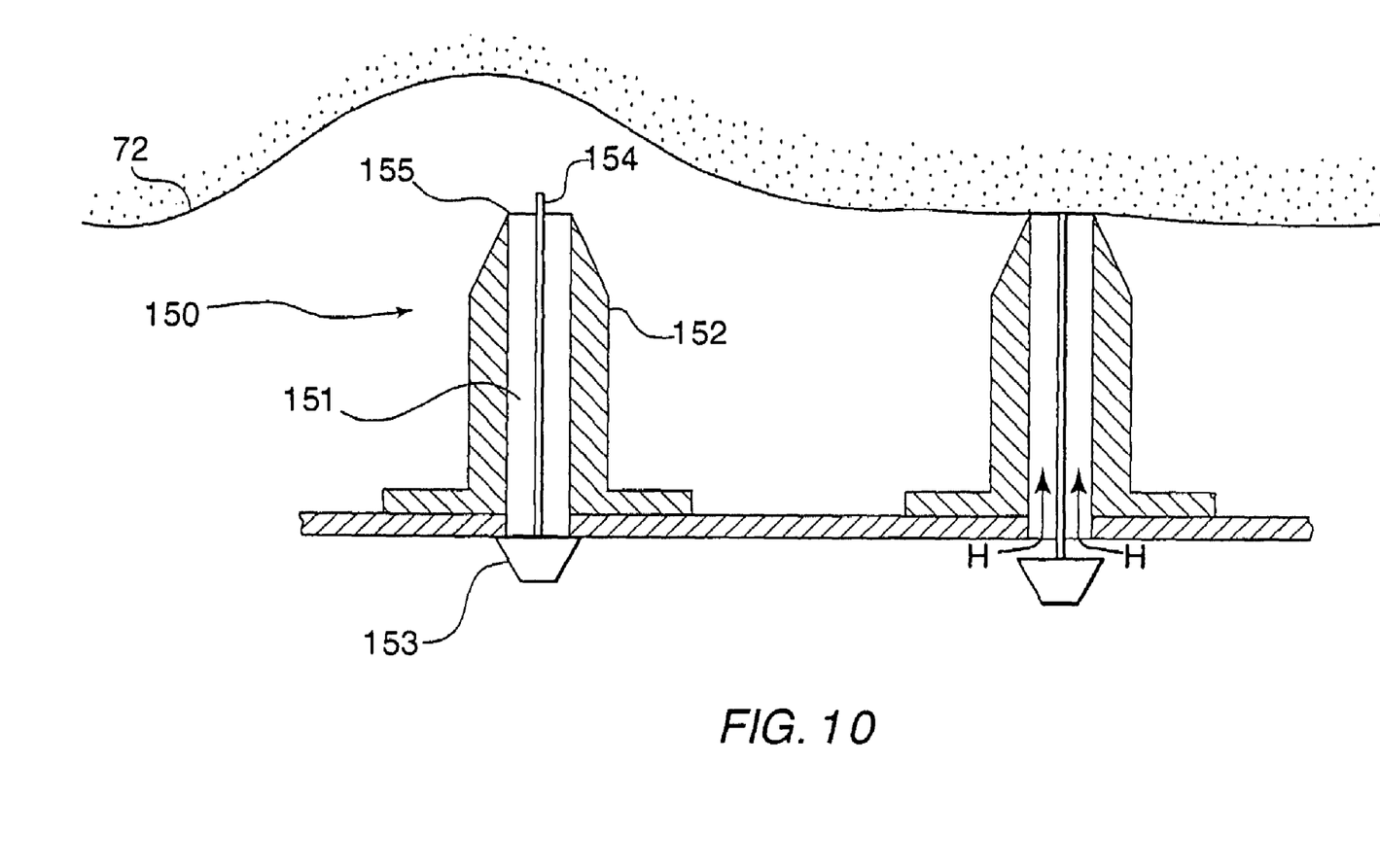
FIG. 10 is an enlarged sectional view of another alternative embodiment of the present invention illustrating injectors and sealing units positioned in an irregularly shaped artery of the patient.

In FIG. 10, another embodiment of sealing unit, designated 150, is shown to accommodate the cylindrical internal passageway 151 of injector 152. Sealing unit 150 comprises seal 153 attached to stem 154. Stem 154 extends beyond the distal end 155 of injector 152, to engage the vessel wall 72. Upon engagement with vessel wall 72, the stem 154 translates radially inward, forcing seal 153 to open, thereby allowing therapeutic fluid to flow into the vessel wall through cylindrical internal passageway 151 of injector 152. Fluid flow arrow H demonstrates the direction of fluid flow. It will be appreciated by one skilled in the art that stem 154 and the geometry of sealing unit 150 may be modified in order to allow therapeutic fluid to flow into the vessel wall only when a predetermined force induced by vessel wall 72, illustrated as pressure force E in FIG. 7, is met.

Also, a cutting edge may be formed or separately attached to the distal end 155 of injector 152 (shown in FIG. 11), the distal end 92 of injector 83 (shown in FIG. 7), or the distal end of stem 154 (shown in FIG. 10). A skilled artisan will appreciate that a variety of cutting devices and injector geometries and shapes would permit puncturing through plaque formed on the interior wall of the vessel without puncturing completely through the vessel wall, so that therapeutic may be delivered into the vessel.

A variety of forces may be utilized to maintain the seal in a position to prevent the flow of therapeutic from an unengaged injector into the bloodstream. In FIG. 7, pressurizing a therapeutic fluid source 85 (not shown) may induce a fluid pressure upon seal 91, thereby maintaining seal 91 in a position blocking the flow of therapeutic from the injector 83 to the vessel wall 72. The force arrow G demonstrates the direction of fluid pressure on seal 91. In another alternate embodiment, seal 91 may be formed such that the drag coefficient of the seal 91 is greater than the drag coefficient of the interior surface of the injector, thereby imparting a viscous drag force induced by the flow of therapeutic fluid around seal 91 of unengaged injector 83 and urging seal 91 radially outward in a position to block the flow of therapeutic. Seal 91 can either be patterned with a rough surface, coated with a surface treatment, or geometrically formed to increase the drag force upon seal 91.

Figure 11:
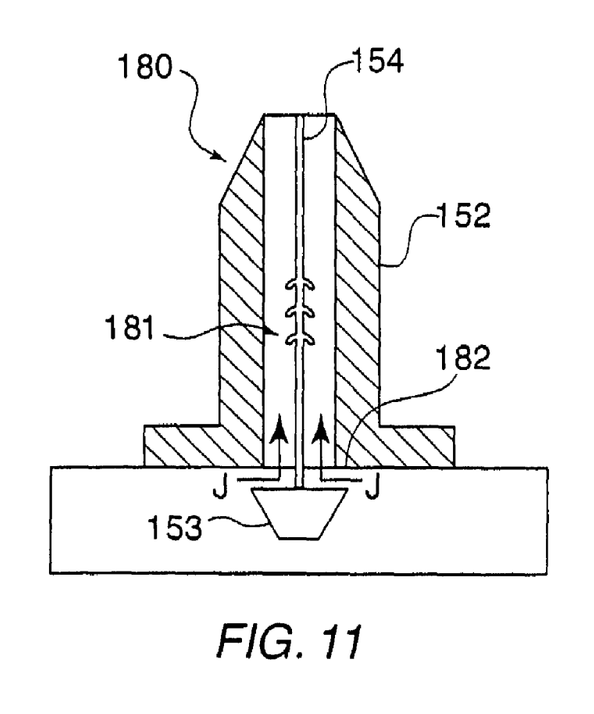
FIG. 11 is an enlarged sectional view of another alternative embodiment of the present invention illustrating injectors and sealing units.
Figure 12:
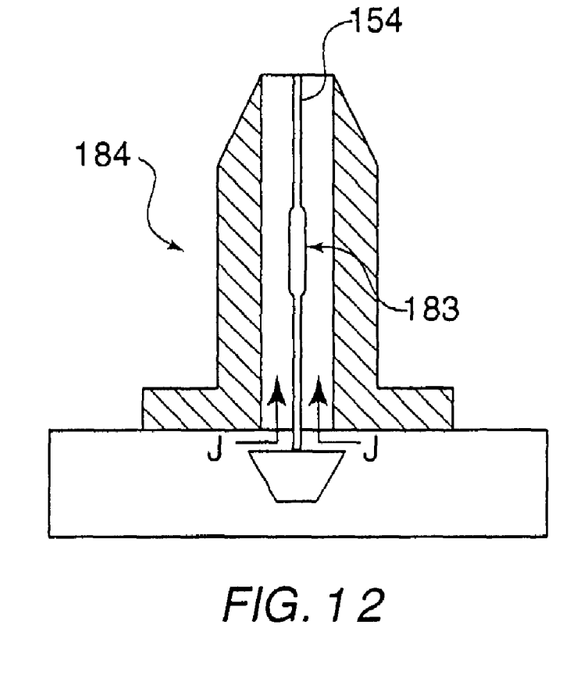
FIG. 12 is an enlarged sectional view of another alternative embodiment of the present invention illustrating injectors and sealing units.

Similarly, sealing unit 150 of FIG. 10 can be modified to increase the viscous drag force urged upon the sealing unit 150, as illustrated in FIG. 11. In FIG. 11, sealing unit 180 is shown comprising stem 154, seal 153, and cups 181. Cups 181 cause a drag force urged upon sealing unit 180 as therapeutic fluid flows around cups 181 in the direction demonstrated by flow arrow J. This force urges sealing unit 180 to translate radially outward thereby sealing the proximal end 182 of injector 152. Although several cups 181 are illustrated in FIG. 11, a skilled artisan would appreciate that one cup may be used to translate sealing unit 180. In another alternative embodiment shown in FIG. 12, sealing unit 184 comprises block 183 attached to stem 154 to cause a drag force urged upon sealing unit 184.

Figure 13:
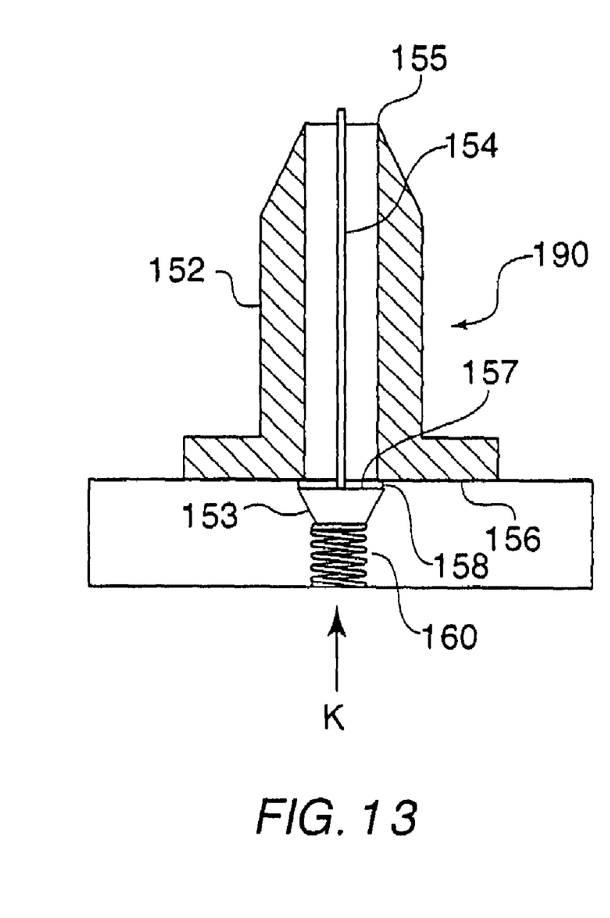
FIG. 13 is an enlarged sectional view of another alternative embodiment of the present invention illustrating injectors and sealing units.
Figure 14:
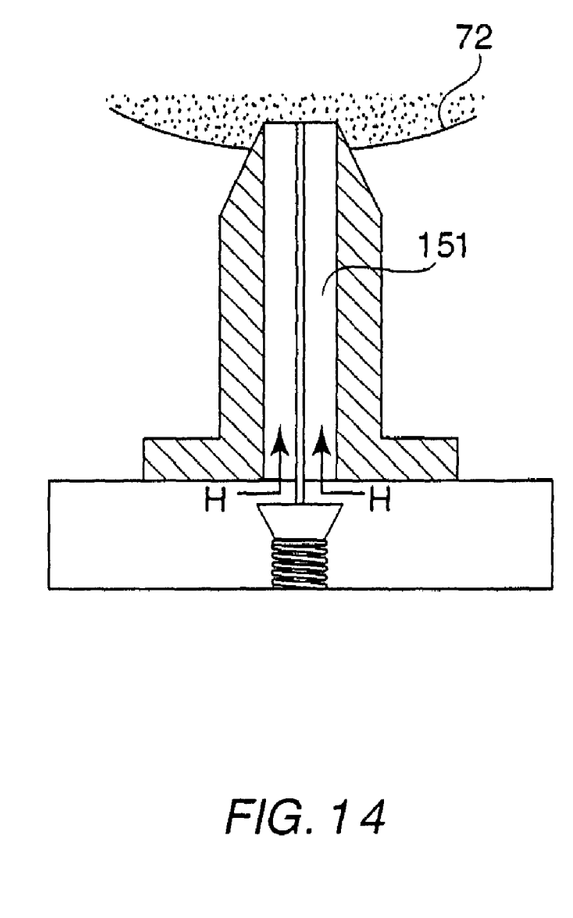
FIG. 14 is an enlarged sectional view of another alternative embodiment of the present invention illustrating engaged injectors and sealing units positioned in an artery of the patient.

In another alternate embodiment, a mechanical force may be used to exert pressure against sealing unit 150. As illustrated in FIG. 13, sealing unit 190 includes spring 160, which can be attached to the exterior surface of inflatable balloon 82 (shown in FIG. 6) to physically communicate with seal 153. Spring 160 exerts a radially outward force upon seal 153 in the direction demonstrated by force arrow K. Accordingly, seal 153 is urged against proximal end 156 of injector 152, and stem 154 extends beyond distal end 155 of injector 152. Sealing unit 190 may also include a compliant gasket 158 attached to exterior surface 157 of seal 153 to assist in sealing seal 153 against proximal end 156 of injector 152. The compliant gasket 158 maybe included in any embodiment of sealing unit 150 described herein. Once injector 152 engages vessel wall 72, as shown in FIG. 14, the pressure force exerted on stem 154 by the vessel wall 72 will overcome the spring force, thereby urging the stem 154 and seal 153 radially inward and permitting flow of therapeutic agents into the vessel wall 72 through the cylindrical internal passageway 151 of injector 152. The direction of flow of therapeutic is demonstrated by directional arrow H. It will be relevant to one skilled in the art that the spring force can be modified by adjusting the spring constant of the spring.

Figure 15:
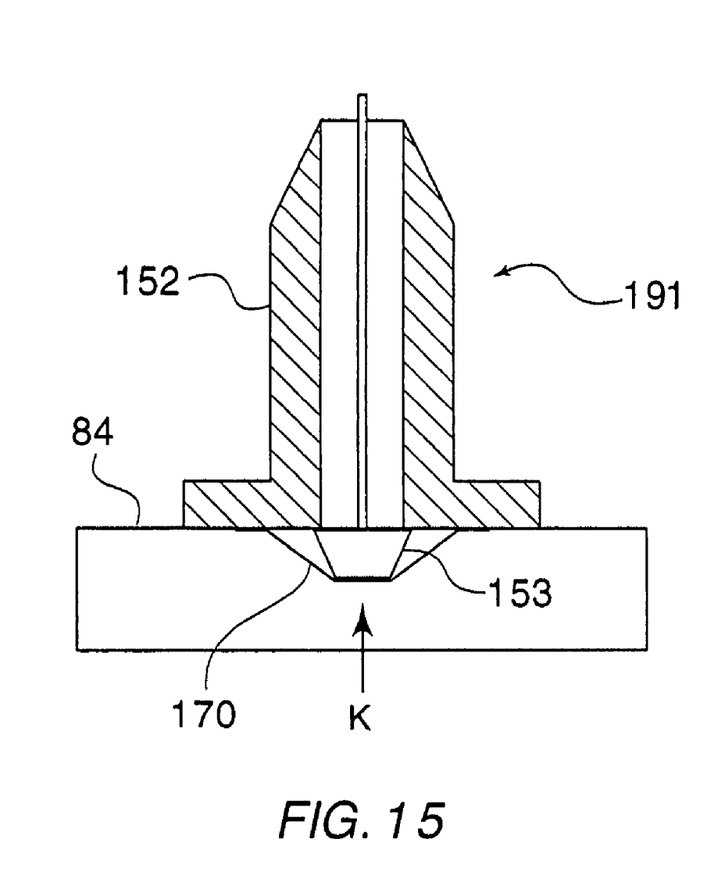
FIG. 15 is an enlarged sectional view of another alternative embodiment of the present invention illustrating injectors and sealing units.
Figure 16:
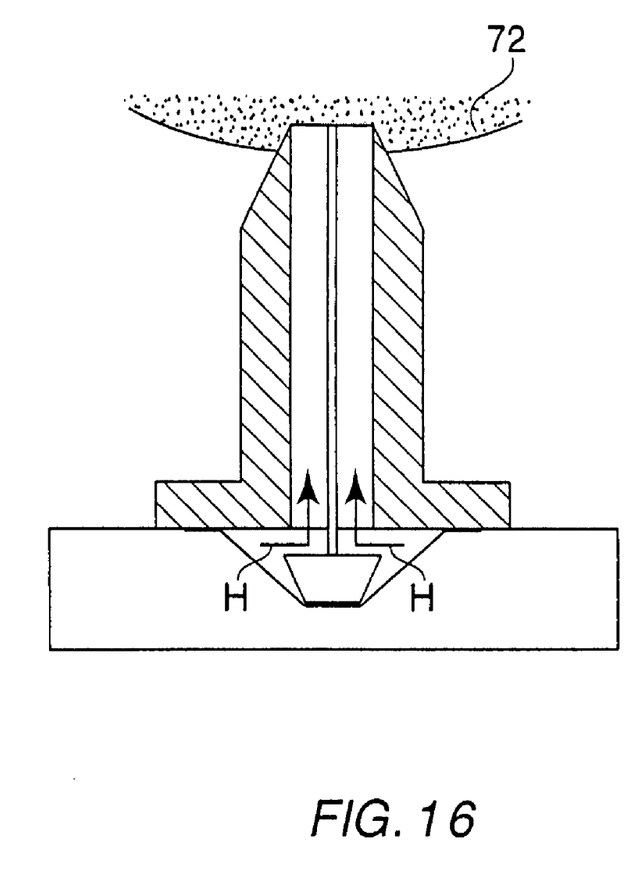
FIG. 16 is an enlarged sectional view of another alternative embodiment of the present invention illustrating engaged injectors and sealing units positioned in an artery of the patient.

Alternatively, mechanical force K may be exerted upon seal 153 by an elastic band 170, as shown in sealing unit 191 of FIG. 15. Elastic band 170 can be attached to the surface of the tubular sleeve 84 or to the base of injector 152. Further, elastic band 170 would be attached as to permit the flow of therapeutic fluid around or through the elastic band 170 when the injector 152 engages the vessel wall. A skilled artisan will know that the force properties of elastic band 170 may be modified such that when the pressure force exerted by the vessel wall 72 on sealing unit 191 overcomes the elastic band force K, the seal 153 is urged radially inward as seen in FIG. 16, thereby permitting flow of therapeutic agents into the vessel wall 72 in the direction demonstrated by directional arrow H. In the alternative embodiments discussed above, the spring 160 and elastic band 170 may be made from numerous materials, including stainless steel, plastic, and other suitably rigid polymers. Further, spring 160 and elastic band 170 can be attached in any manner well known in the pertinent art, such as by bonding or other mechanical attachment means.

In still another embodiment, other forces, such as chemical or static forces, may also be used to prevent the flow of fluid through the injectors. The seal can be initially maintained in a sealed position against the injector by bonding the seal to the injector's orifice. The seal would seal the unengaged injector while the balloon inflates. However, when the injector engages and embeds into the vessel wall, the pressure force of the vessel wall would overcome the bond strength of the bonding agent, thereby translating the seal away from the injector's orifice and permitting therapeutic to flow into the vessel wall. The bond may be an adhesive bond, an electrostatic bond, chemical bond, or other bonding agents known in the pertinent art.

The term "therapeutic" as used throughout includes one or more "therapeutic agents" or "drugs." The terms "therapeutic" and "drugs" are used interchangeably herein and include pharmaceutically active compounds, nucleic acids with and without carrier vectors such as lipids, compacting agents (such as histones), virus (such as adenovirus, adenoassociated virus, retrovirus, lentivirus and α-virus), polymers, hyaluronic acid, proteins, cells and the like, with or without targeting sequences. The therapeutics administered in accordance with the invention includes the therapeutic agent(s) and solutions thereof.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1("VP22")), and viral liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetylsalicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin ; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, h-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoaffractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

The therapeutic delivery catheter may be used, for example, in any application for treating, preventing, or otherwise affecting the course of a disease or tissue or organ dysfunction. For example, the methods of the invention can be used to induce or inhibit angiogenesis, as desired, to prevent or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

One of skill in the art will realize that the examples described and illustrated herein are merely illustrative, as numerous other embodiments may be implemented without departing from the spirit and scope of the present invention.

What is claimed is:

1. A device for delivering fluid into a vessel wall comprising:
    a catheter having at least one internal lumen;
    an inflatable balloon in fluid communication with at least one internal lumen of the catheter and having an exterior surface;
    at least one injector mounted on the exterior surface of the inflatable balloon in fluid communication with at least one internal lumen of the catheter, wherein the injector comprises
        a hollow protrusion having a first end and a second end, and
        a fluid channel; and
    a sealing unit having a seal for sealing the fluid channel of the injector wherein the seal seals the second end of the hollow protrusion and the seal selectively translates when the sealing unit engages the vessel wall from a first position to a second position.

2. The device of claim 1 wherein the seal is substantially spherical in shape.

3. The device of claim 1 wherein the first position is an injector sealing position and the second position is an injector opening position.

4. A device for delivering fluid into a vessel wall comprising:
    a catheter having at least one internal lumen;
    an inflatable balloon in fluid communication with at least one internal lumen of the catheter and having an exterior surface;
    at least one injector, having a fluid channel and mounted on the exterior surface of the inflatable balloon, in fluid communication with at least one internal lumen of the catheter; and
    a sealing unit having a seal wherein the sealing unit resists fluid flowing adjacent the sealing unit thereby inducing a force on sealing unit, urging the sealing unit to translate, and seal the fluid channel of the injector.

5. The device of claim 4 wherein the sealing unit is coated.

6. The device of claim 4 wherein the seal is coated.

7. The device of claim 4 wherein the sealing unit is patterned.

8. The device of claim 4 wherein the seal is patterned.

9. A device for delivering fluid into a vessel wall comprising:
    a catheter having at least one internal lumen;
    an inflatable balloon in fluid communication with at least one internal lumen of the catheter and having an exterior surface;
    at least one injector, having a fluid channel and mounted on the exterior surface of the inflatable balloon, in fluid communication with at least one internal lumen of the catheter;
    a sealing unit having a seal; and
    a mechanical system having an elastic band for applying a force urging the seal to seal the fluid channel of the injector.

10. A device for delivering fluid into a vessel wall comprising:
    a catheter having at least one internal lumen;
    an inflatable balloon in fluid communication with at least one internal lumen of the catheter and having an exterior surface;
    at least one injector, having a fluid channel and mounted on the exterior surface of the inflatable balloon, in fluid communication with at least one internal lumen of the catheter;
    a sealing unit having a seal wherein the seal selectively translates when the sealing unit engages the vessel wall from a first position to a second position; and
    a bond for maintaining the seal in a sealed position against the injector to seal the fluid channel of the injector.

11. The device of claim 10 wherein the bond is an adhesive bond.

12. The device of claim 10 wherein the bond is an electrostatic bond.

13. The device of claim 10 wherein the bond is a chemical bond.

14. The device of claim 10 wherein the first position is an injector sealing position and the second position is an injector opening position.

* * * * *